United States Patent
Seeber et al.

(10) Patent No.: US 9,795,454 B2
(45) Date of Patent: Oct. 24, 2017

(54) HOLDING AND POSITIONING APPARATUS OF A SURGICAL INSTRUMENT AND/OR AN ENDOSCOPE FOR MINIMALLY INVASIVE SURGERY AND A ROBOTIC SURGICAL SYSTEM

(71) Applicant: avateramedical GmbH, Jena (DE)

(72) Inventors: Marcel Seeber, Jena (DE); Andreas Karguth, Tüttleben (DE); Christian Trommer, Wipfratal/Schmerfeld (DE)

(73) Assignee: avateramedical GmbH, Jena (DE)

( * ) Notice: Subject to any disclaimer, the term of this patent is extended or adjusted under 35 U.S.C. 154(b) by 137 days.

(21) Appl. No.: 14/653,212

(22) PCT Filed: Dec. 12, 2013

(86) PCT No.: PCT/DE2013/000803
§ 371 (c)(1),
(2) Date: Jun. 17, 2015

(87) PCT Pub. No.: WO2014/094716
PCT Pub. Date: Jun. 26, 2014

(65) Prior Publication Data
US 2016/0184030 A1    Jun. 30, 2016

(30) Foreign Application Priority Data

Dec. 20, 2012 (DE) .......................... 10 2012 025 099
Mar. 14, 2013 (DE) .......................... 10 2013 004 459

(51) Int. Cl.
*A61B 34/30*    (2016.01)
*B25J 18/00*    (2006.01)
(Continued)

(52) U.S. Cl.
CPC .............. *A61B 34/30* (2016.02); *A61B 90/11* (2016.02); *A61B 90/50* (2016.02); *B25J 18/007* (2013.01);
(Continued)

(58) Field of Classification Search
None
See application file for complete search history.

(56) References Cited

U.S. PATENT DOCUMENTS

| | | | |
|---|---|---|---|
| 2007/0137371 A1 | 6/2007 | Devengenzo et al. | |
| 2007/0250078 A1* | 10/2007 | Stuart .................... | A61B 34/37 606/130 |
| 2011/0071473 A1* | 3/2011 | Rogers ............... | A61B 1/00149 604/167.01 |

FOREIGN PATENT DOCUMENTS

| | | |
|---|---|---|
| CN | 101340852 A | 1/2009 |
| CN | 102510740 A | 6/2012 |

(Continued)

*Primary Examiner* — Erica Lee
(74) *Attorney, Agent, or Firm* — Christensen, Fonder, Dardi & Herbert PLLC

(57) ABSTRACT

The invention describes a retaining and positioning device of a surgical instrument and/or of an endoscope for minimally invasive surgery, more particularly for use within a surgical robot system, including a first axis of rotation, around which a retaining element can be rotated. The first axis of rotation always intersects with a longitudinal axis of at least one surgical instrument and/or of an endoscope in a pivotal point by means of a thrust drive being attached to the retaining element, to which thrust drive an instrument drive unit can be rotatably arranged around the pivotal point. The instrument drive unit has a telescopic arrangement via which the surgical instrument can be moved in a translational manner along the longitudinal axis thereof by means of a guide arrangement in the body in such a manner that the (Continued)

longitudinal axis of the surgical instrument is variably adjustable relative to the telescopic arrangement.

13 Claims, 21 Drawing Sheets

(51) Int. Cl.
*A61B 90/50* (2016.01)
*A61B 90/11* (2016.01)

(52) U.S. Cl.
CPC ... *A61B 2034/301* (2016.02); *A61B 2034/302* (2016.02); *A61B 2034/305* (2016.02)

(56) References Cited

FOREIGN PATENT DOCUMENTS

| EP | 2 332 484 A2 | 6/2011 |
|----|--------------|--------|
| WO | WO 2007/075864 A1 | 7/2007 |
| WO | WO 2011/037718 A1 | 3/2011 |
| WO | WO 2012/044869 A2 | 4/2012 |

\* cited by examiner

HOLDING AND POSITIONING APPARATUS OF A SURGICAL INSTRUMENT AND/OR AN ENDOSCOPE FOR MINIMALLY INVASIVE SURGERY AND A ROBOTIC SURGICAL SYSTEM

PRIORITY CLAIM

The present application is a National Phase entry of PCT Application No. PCT/DE2013/000803, filed Dec. 12, 2013, which claims priority from German Patent Application Number 102012025099.1, filed Dec. 20, 2012, and German Patent Application Number 102013004459.6, filed Mar. 14, 2013, the disclosures of which are hereby incorporated by reference herein in their entirety.

FIELD OF THE INVENTION

The present invention relates to a holding and positioning apparatus of a surgical instrument and a robotic surgical system or telemanipulator for minimally invasive surgery and in particular for laparoscopy.

BACKGROUND OF THE INVENTION

Robotic systems or telemanipulators for minimally invasive surgery, in particular for laparoscopic surgery, are replacing the operating instruments usually guided manually by the surgeon, such as, for example, surgical instruments, endoscope and camera, with a motorized positioning. The operating instruments to be used are guided into the inside of a patient via one or more trocars. Trocar denotes an instrument using which the surgeon in minimally invasive surgery creates an access to the body cavity of the patient (usually the abdomen or the chest cavity), wherein the access is held open by a tube. The mounting of movement mechanics and control logic provided in the robotic system enables the movement of the operating instruments about a pivot point in 2 degrees of freedom (x, y) as well as a translational movement of the operating instruments along the instrument axis (z). The invariant point of the movement in 2 degrees of freedom (x, y) is called the pivot point. This pivot point ideally lies in or near the penetration point of the trocar through the patient's abdominal wall. The control logic of a robotic system must know the pivot point, or the pivot point must be defined by the structural design of the movement mechanics, in order to restrict a movement of the operating instrument such that the biomechanical stress on the tissue around the trocar is as low as possible.

Robotic systems known from the state of the art are based on robotic arms with an active movement of an operating instrument which, on the one hand, require a large installation space and wherein, because of the typical embodiments, it is difficult to avoid collisions as a result of the movement sequences of the robotic arms.

During a minimally invasive surgical procedure at least two, as a rule, three to four surgical instruments, such as graspers, scissors, needle holders, dissectors, as well as a camera or an endoscope, are used, each of which is guided into the inside of the patient's body via a separate trocar. This means that, for each operating instrument used, there is a robotic arm which controls the positions of the robotic arms and the active movement of the instrument.

SUMMARY OF THE INVENTION

A disadvantage of the solutions from the state of the art is that, due to the large space required by the structure, the positionability of the instruments is limited and access to the patient by theater staff, e.g., the assisting doctor and the theater nurse, is only possible to a limited extent.

A further disadvantage is that the invariant point in known systems is always necessarily formed by a mechanical coupling between trocar and robotic arm.

An object of the present invention is therefore to provide a manipulator arm for positioning a surgical instrument and a robotic surgical system which provides high variability and requires only little installation space and is smaller and simpler in its design and optionally makes it possible either to couple the trocar to the manipulator arm mechanically or manages without this mechanical coupling of the trocar to the manipulator arm.

A further object of the present invention is to provide a robotic system which offers a larger range for adjusting the pre-positioning for a holding apparatus of a manipulator arm.

When using two or more holding apparatuses for manipulator arms more flexible positioning possibilities relative to each other are thus possible.

These objects are achieved by the present invention according to the features of claim 1 by a holding and positioning apparatus of a surgical instrument and/or of an endoscope for minimally invasive surgery, in particular for use within a robotic surgical system, which comprises a first axis of rotation around which a holding element is rotatably arranged, wherein the first axis of rotation always intersects with the longitudinal axis of at least one surgical instrument and/or of an endoscope in a pivot point in that a linear actuator is attached to the holding element, which linear actuator arranges an instrument drive unit in a rotatable manner around the pivot point, and wherein a telescopic device is provided on the instrument drive unit, by means of which the surgical instrument and/or the endoscope can be moved in a translational manner along its longitudinal axis by means of a guide device into the body such that the longitudinal axis of the surgical instrument and/or of the endoscope is variably adjustable relative to the telescopic device.

The objects are further achieved by the present invention according to the features of claim 11 by a robotic surgical system with several robotic arms, on which at least one surgical instrument and/or one endoscope for minimally invasive surgery can be arranged, at least two holding and positioning apparatuses are attached on a holding support system running substantially transverse to the holding and positioning apparatuses, wherein the holding support system is constructed from in each case one coupling point for each holding and positioning apparatus, and wherein the coupling points are connected to each other in each case rigidly or via joints.

Further advantageous embodiments of the invention as well as of the robotic surgical system according to the invention result from the dependent claims, analogous to the manipulator arm for the active positioning for a surgical instrument. This is shown in particular by the fact that the manipulator arm according to the invention for the active positioning of a surgical instrument can be combined or retrofitted with a robotic system. According to the invention the terms robotic system and telemanipulator can be used synonymously.

It is advantageous if the instrument drive unit is rotatably mounted on the telescopic device by means of an instrument pivotal point such that the telescope longitudinal axis of the telescopic device is variable relative to the longitudinal axis of the surgical instrument and/or of the endoscope in dependence on the linear actuator.

A further embodiment of the invention is designed such that the telescopic device has several telescopic elements, wherein the instrument pivotal point is arranged on the telescopic element which has the largest range of adjustment.

According to a preferred embodiment, the guide device has at least one instrument guide through which the shaft of the surgical instrument and/or of the endoscope extends.

A particular advantage is that the linear actuator is attached to the telescopic device by means of a linear actuator position point such that the rotational movement of the instrument support unit about the pivot point results in a coupling device having a coupling pivotal point which is rigidly connected to the holding element. The rotation of the instrument support unit with the instruments and/or an endoscope both about the pivot point and also about the coupling pivotal point makes it possible for the holding element to be arranged substantially steady relative to the pivot point.

According to a preferred embodiment the holding and positioning apparatus is configured such that the instrument drive unit moves the surgical instrument and/or the endoscope in several degrees of freedom, wherein the instrument drive unit is controlled by the surgeon via a control unit by means of control and supply lines which are guided through the holding element and the linear actuator.

The first axis of rotation is, in particular, formed in that a drive unit is provided which controls the surgical instrument and/or endoscope, wherein the drive unit can be attached to a robotic arm and wherein a pivot joint is provided between the drive unit and the holding element.

A further embodiment is designed such that a coupling element is attached to the holding element, which is rotatably connected at the distal end at the pivot point to an instrument guide. By this means, the pivot point is additionally mechanically predefined with respect to the holding element, with the result that an additional fixing of the pivot point is made possible.

Moreover, the present invention can be extended in that several surgical instruments are guided into the inside of the body through a single trocar, wherein a separate instrument drive unit is provided for each surgical instrument, and wherein in particular the surgical instruments are designed curved in the longitudinal direction.

If the holding element can be adapted in its starting position by means of a pre-positioning device, wherein the pre-positioning device has one or more pre-positioning elements, which in each case can be pre-set in their position via at least one axis of rotation, wherein in particular four pre-positioning elements can be pre-set with positions which are variable with respect to each other in series, the holding and positioning apparatus can be pre-set in a desired position.

The robotic surgical system according to the invention can further be developed in that the holding support system is connected by means of a coupling support connection to a substantially vertically running main support device for support in relation to a fixed bearing, which can be arranged to be movable or is predefined with respect to a fixed or mobile operating table.

According to a further embodiment of the invention the robotic surgical system has a central control unit which is connected to each of the holding and positioning apparatuses with the corresponding surgical instruments and/or endoscopes and is coupled to an operating unit for the input of commands in the form of control data of a surgeon, which operating unit displays image data from one or more endoscopes by means of a visualization unit.

In addition, it is advantageous that the control unit and the operating unit are coupled to a mobile operating table, wherein both the image data and the control data are processed in dependence on the predetermined positions of the holding and positioning apparatus as well as of the operating table.

BRIEF DESCRIPTION OF THE FIGURES

The present invention is realized purely by way of example by the attached figures, which:

FIG. 3a is a schematic view of the manipulator arm according to the invention for the active positioning of a surgical instrument which is connected to a telescopic extension via a pivot-mounted drive unit, without the coupling element according to FIG. 1a;

DETAILED DESCRIPTION

Figure 1A:
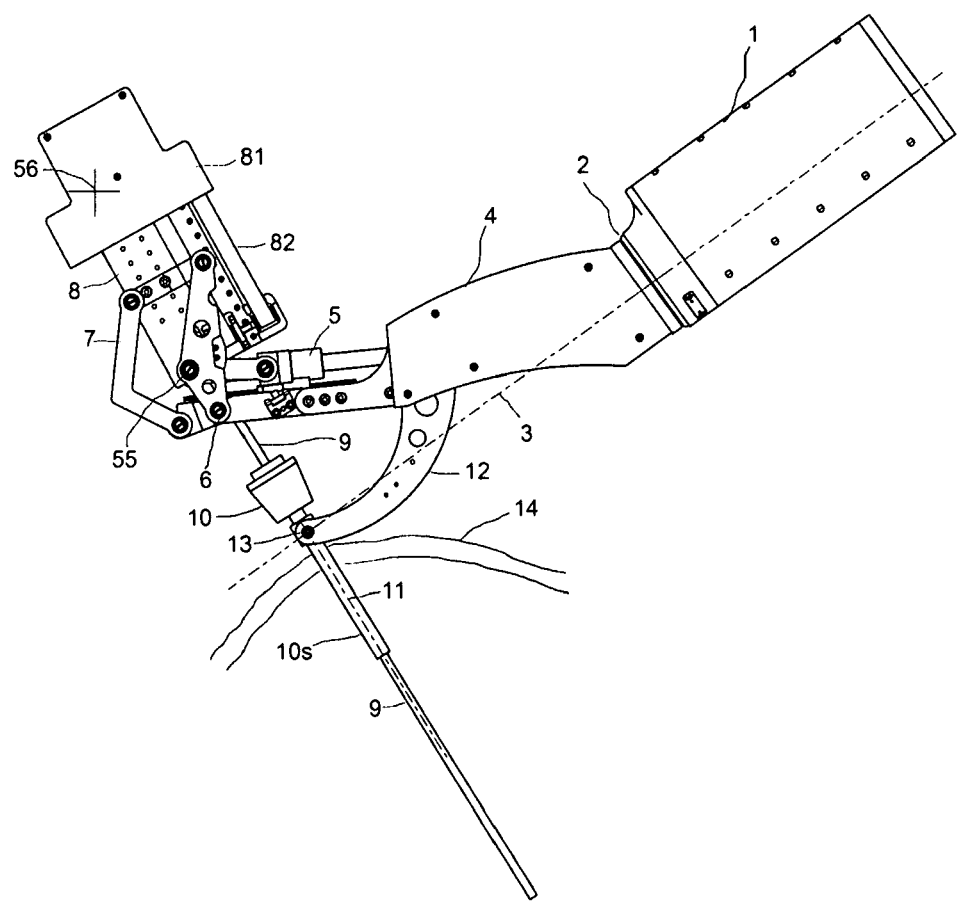
FIG. 1a is a schematic view of the manipulator arm according to the invention for the active positioning of a surgical instrument which is connected to a telescopic extension via a pivot-mounted drive unit, including the coupling element between the guide device for guiding a surgical instrument through and the structural apparatus for realizing the second axis of rotation.
Figure 1B:
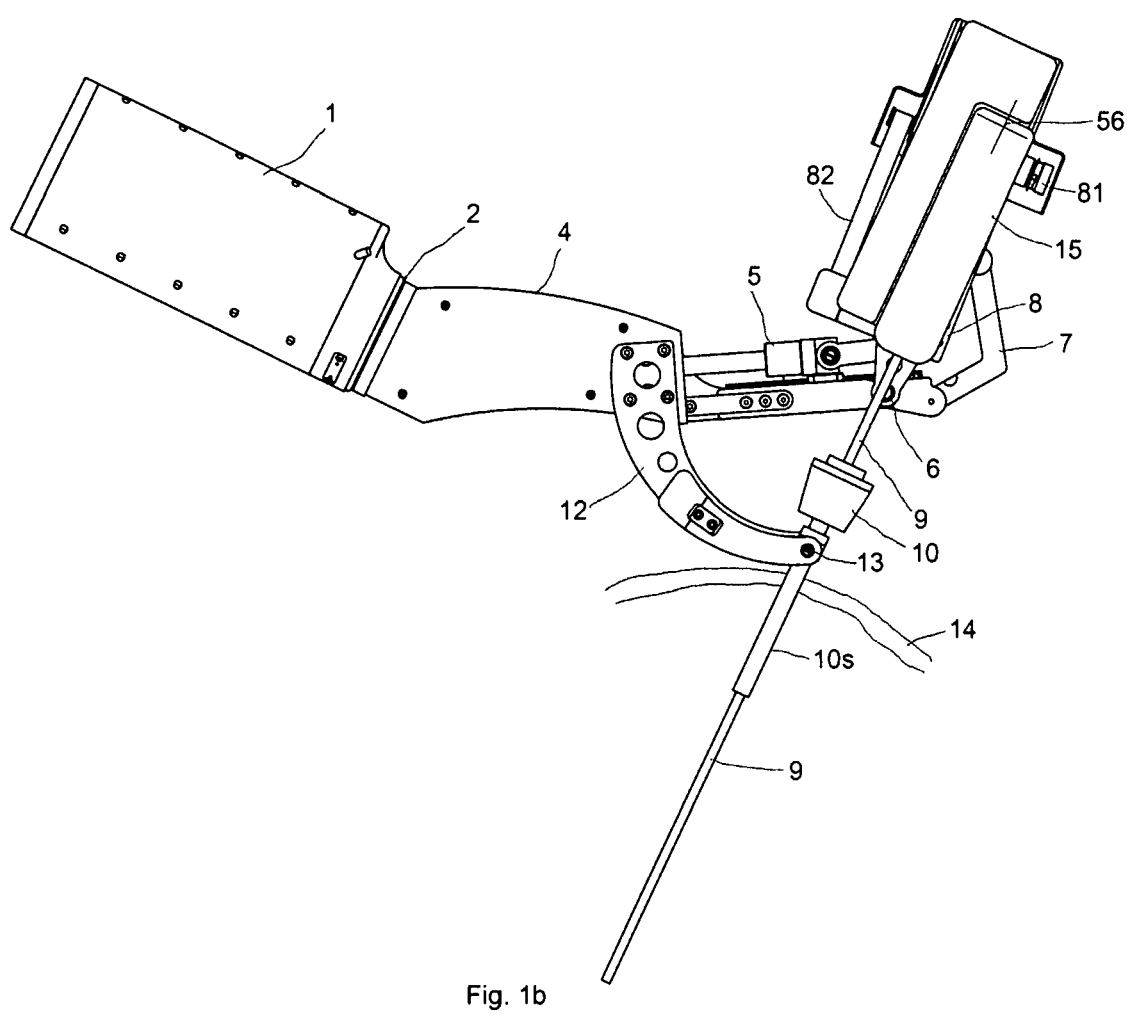
FIG. 1b is a schematic view of the manipulator arm according to the invention for the active positioning of a surgical instrument which is connected to a telescopic extension via a pivot-mounted drive unit, including the coupling element between the guide device for guiding a surgical instrument through and the structural apparatus for realizing the second axis of rotation.

The present invention is described below in detail by way of example with reference to the figures:

FIG. 1a, FIG. 2a, FIG. 1b and FIG. 2b show a manipulator arm according to the invention for the active positioning of a surgical instrument 9 including the coupling element 12 between the guide device 10 for guiding a surgical instrument 9 through and the structural apparatus 4 for realizing the second axis of rotation. During a minimally invasive laparoscopic procedure, as a rule four operating instruments are used, of which three are surgical instruments and one is a camera or endoscope, which are controlled by the surgeon via the telemanipulator system. According to the invention, four designs of a manipulator arm are therefore preferably present in the system. It is understood, however, that embodiments with one to three or more than four manipulator arms can also be provided according to the present invention, wherein each manipulator arm has at least one holding and positioning apparatus according to the invention. Each manipulator arm has the degree of freedom 3 to realize pivot movements of an instrument 9, coupled via an instrument drive unit 15, in the x and y direction as well as for a translational movement in the z direction. For this, each manipulator arm consists of a first drive unit 1, which, via the pivot joint 2, makes possible a rotational movement of at least ±120° about the axis of rotation 3 starting from the zero-point position. This rotational movement about the axis of rotation 3 leads to a tilting of the coupled structural apparatus consisting of the elements 4, 5, 6, 7, 8, 12 about an invariant point 13, the so-called pivot point. The holding element 4 carries a linear actuator 5, which realizes a second rotational movement about a second pivotal point 6, orthogonal to the axis of rotation 3. The coupling element 12 between the holding element 4 and the leadthrough 10 for a surgical instrument 9 is connected to the leadthrough 10 at the pivot point 13 such that the axis of rotation 3 goes through this pivot point 13 and the leadthrough 10 is positively driven to carry out the tilting about the axis of rotation 3. The leadthrough 10 realizes the access through the abdominal wall 14 of a patient for a surgical instrument 9. A power transmission to a coupling guide 7 takes place via a linear actuator 5 in the pivotal point 55, which realizes a rotation of the coupling guide 7 about the pivotal point 6 by at least ±60°. In particular, the leadthrough 10 serves as guide device for the surgical instrument 9 and has a guide shaft 10s which serves as instrument guide of the instrument 9 and preferably is formed in one piece with the leadthrough 10.

A telescopic extension 8 is arranged on the coupling guide 7. The telescopic extension 8 has an actuating drive 81. The supply and control lines for the actuating drive 81 of the telescopic extension 8 are guided along the linear actuator 5 through the holding element 4 and the drive unit 1. The supply and control lines for the linear actuator 5 are guided through the holding element 4 and the drive unit 1.

Figure 2A:
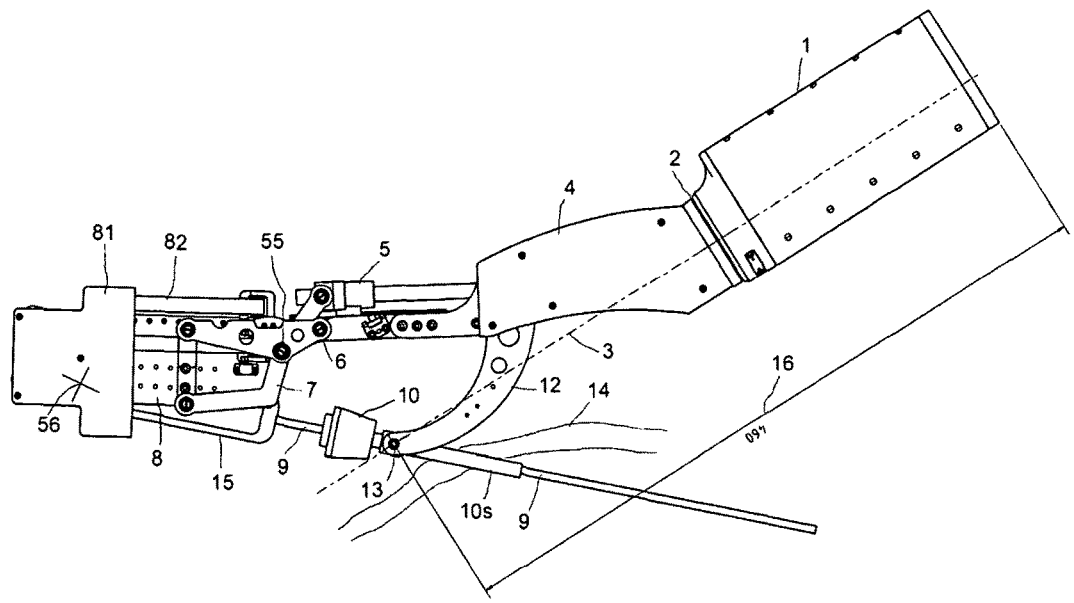
FIG. 2a is a further schematic view of the manipulator arm according to the invention for the active positioning of a surgical instrument which is connected to a telescopic extension via a pivot-mounted drive unit, including the coupling element between the guide device for guiding a surgical instrument through and the structural apparatus for realizing the second axis of rotation, from which can be seen the translatory motion for creating the rotational movement by means of a coupling joint about the second axis of rotation.
Figure 2B:
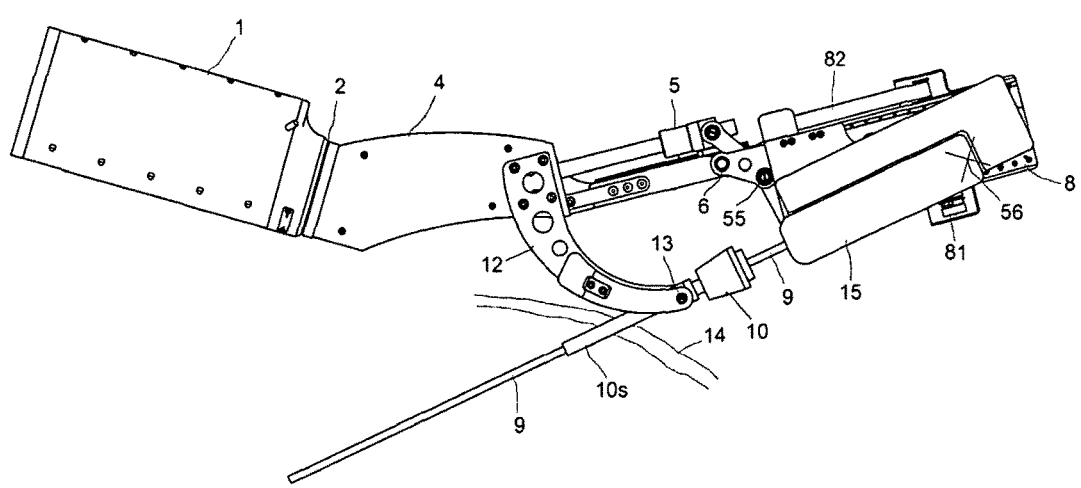
FIG. 2b is a further schematic view of the manipulator arm according to the invention for the active positioning of a surgical instrument which is connected to a telescopic extension via a pivot-mounted drive unit, including the coupling element between the guide device for guiding a surgical instrument through and the structural apparatus for realizing the second axis of rotation, from which can be seen the translatory motion for creating the rotational movement by means of a coupling joint about the second axis of rotation.

An instrument drive unit 15 is rotatably arranged on the telescopic extension 8, as can be seen from FIGS. 2a and 2b. The instrument drive unit 15 serves to realize the degree of freedom of an instrument 9 coupled thereon. For this, an instrument drive unit 15 is equipped with corresponding actuating drives. The supply and control lines for the actuating drives of the instrument drive unit 15 are guided via the telescopic extension 8 along the linear actuator 5 through the holding element 4 and the drive unit 1.

Tilting the coupling element 7 leads to a tilting movement of the telescopic extension 8 fixed thereon about the axis of rotation 6 and thus to a tilting of the instrument drive unit 15 and of the surgical instrument 9 coupled thereon. This leads to a tilting movement of the leadthrough 10 in an axis orthogonal to the axis of rotation 3 about the pivot point 13 (see FIG. 2a). The resulting position of the instrument longitudinal axis 11 corresponds to the axis between an instrument pivotal point 56 of the instrument drive unit 15 on the telescopic extension 8 and the pivot point 13. The surgical instrument 9 is positively driven by means of the leadthrough 10 along the instrument longitudinal axis 11 such that a pivotal tilting movement of the surgical instrument 9 about the pivot point 13 in axes lying orthogonal with respect to each other is realized by means of the drives 1 and 5. A telescopic extension 8 is arranged on the coupling guide 7 such that the surgical instrument 9 fixed to the telescopic extension 8 by means of the instrument drive unit 15 can be displaced along the instrument longitudinal axis 11 through the leadthrough 10 and thus relative to the abdominal wall 14. The whole structural design can be realized to be extremely compact. Surgical instruments 9 typically have a diameter of from 5 to 10 mm and a length of from 250 to 300 mm. The embodiment according to the invention of the telescopic extension 8 is designed such that a surgical instrument 9 can be displaced by preferably at least 250 mm along its instrument longitudinal axis 11 relative to the leadthrough 10 and such that, in the case of the maximum retraction depth of the surgical instrument 9 into the leadthrough 10, the telescopic extension 8 has its smallest length, i.e., only projects insignificantly over the proximal end of the surgical instrument 9, and thus the danger of collision between different surgical instruments 9 and telescopic extensions 8 of manipulator arms arranged next to each other because of the pivotal movements to be carried out is minimized. The whole structural design has a significantly smaller installation space requirement compared with the state of the art. The complete overall length 16 of a manipulator arm according to the invention measured from the drive unit 1 to the pivot point 13 is preferably less than 500 mm. The embodiment with the coupling element 12 for positively driving the pivot point 13 on the leadthrough 10 makes it possible also to use the manipulator arm according to the invention in open operations which are not carried out in a minimally invasive manner.

Figure 3A:
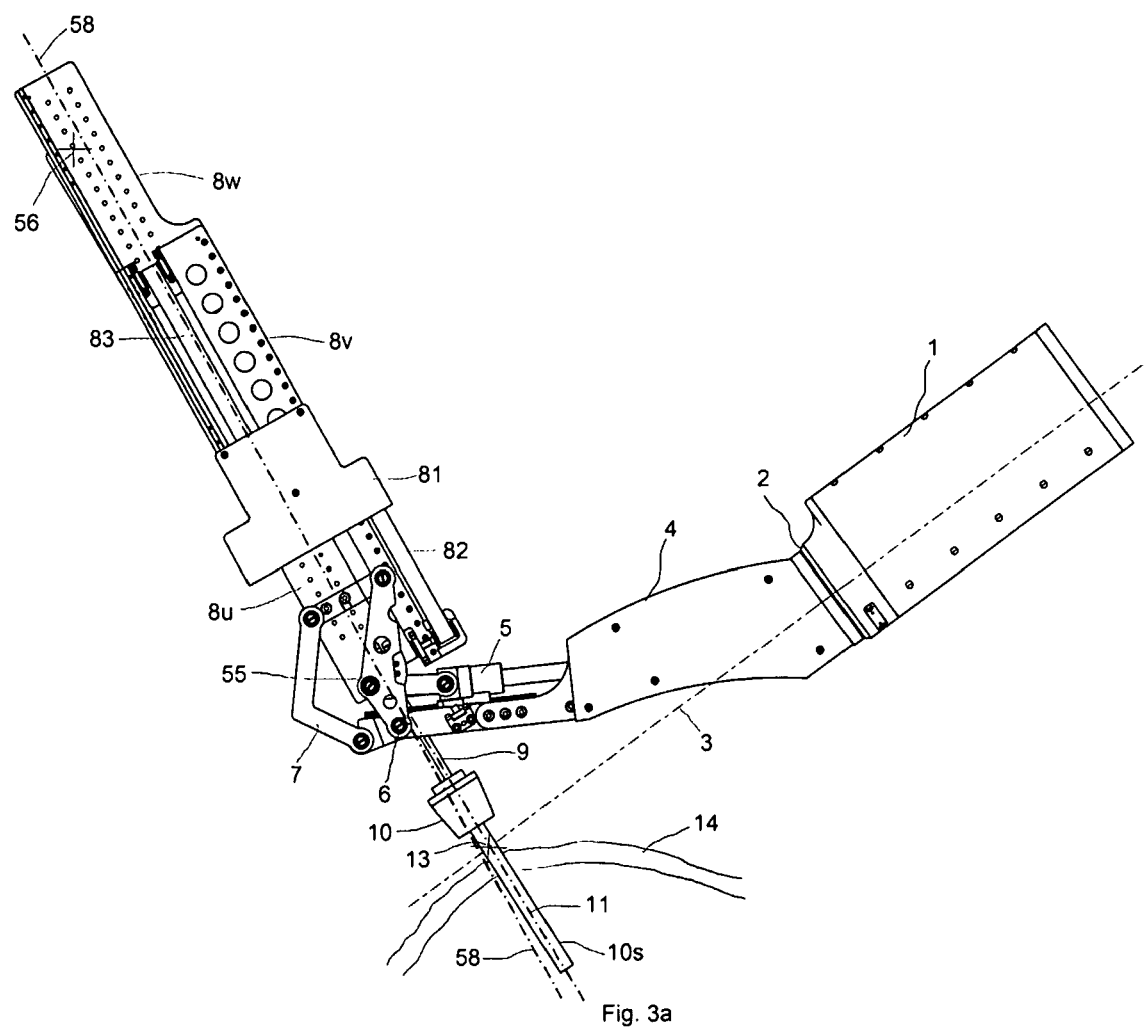
Figure 3B:
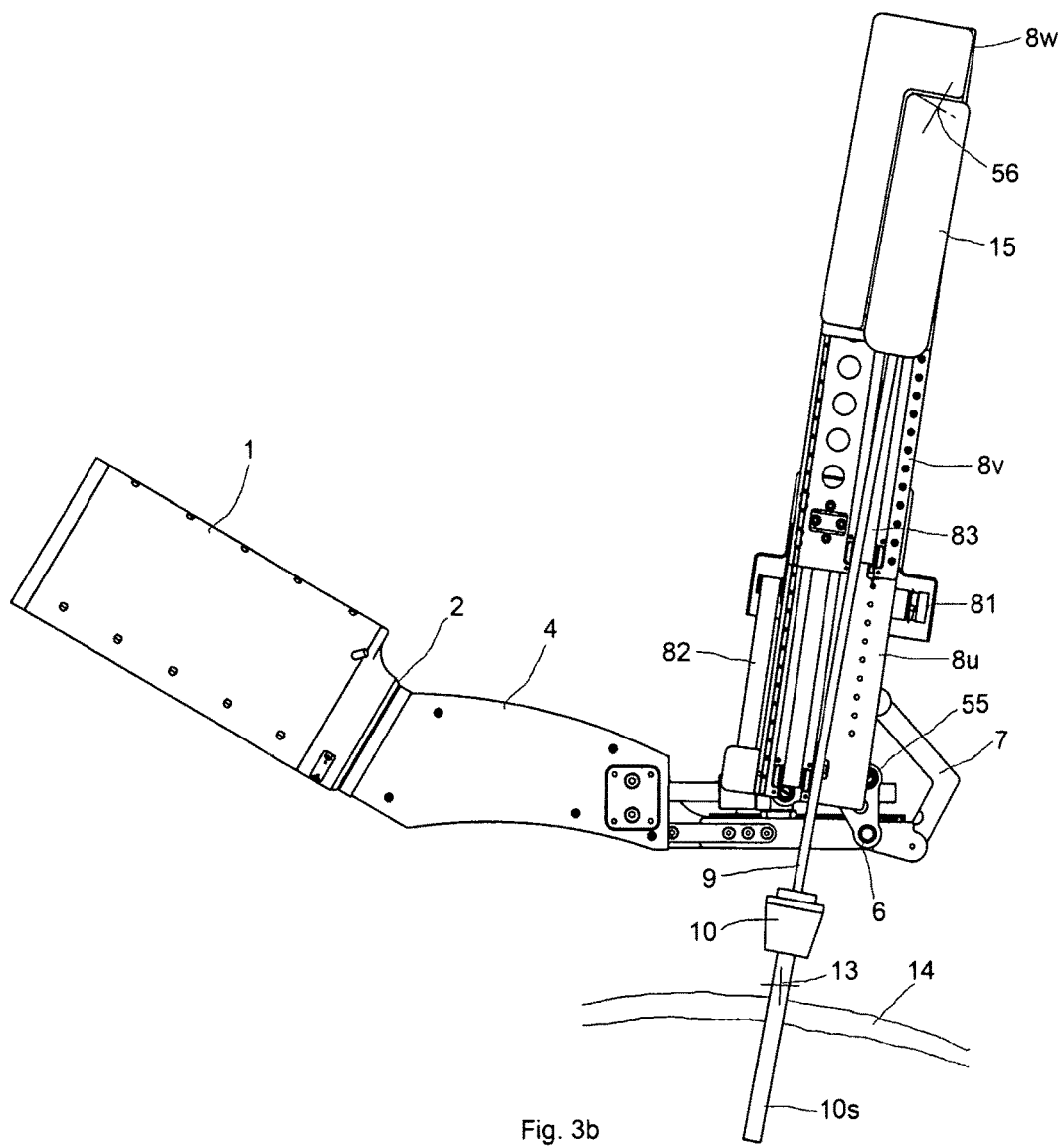
FIG. 3b is a schematic view of the manipulator arm according to the invention for the active positioning of a surgical instrument which is connected to a telescopic extension via a pivot-mounted drive unit, without the coupling element according to FIG. 13.
Figure 4:
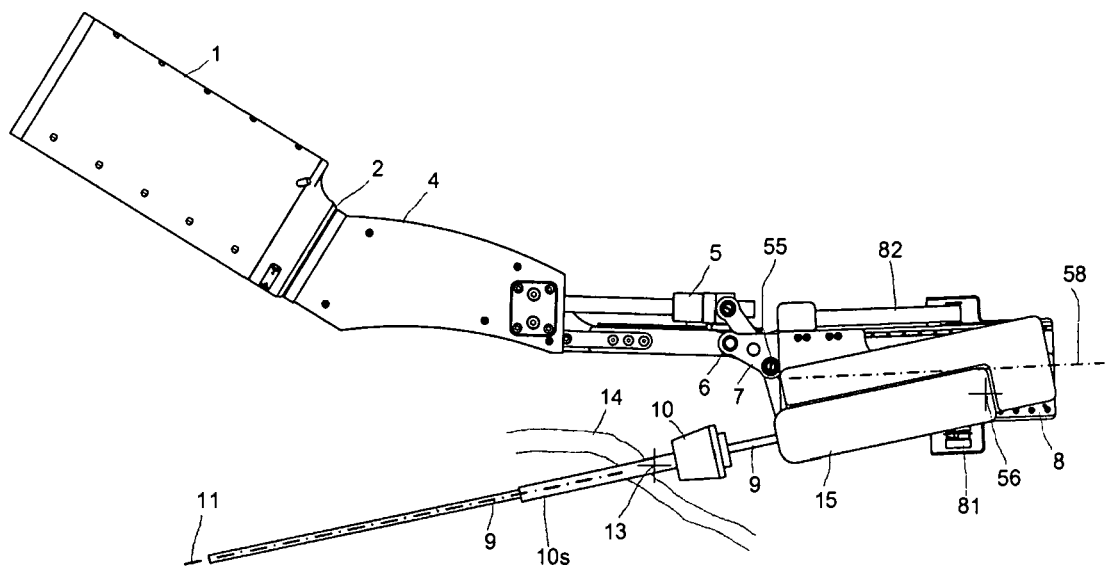
FIG. 4 is a schematic view of the manipulator arm according to the invention for the active positioning of a surgical instrument without the coupling element according to FIG. 1, from which can be seen the translatory motion for creating the rotational movement by means of a coupling joint about the second axis of rotation as well as the coupling of the instrument drive unit.

FIG. 3a, FIG. 3b and FIG. 4 show a manipulator arm according to the invention for the active positioning of a surgical instrument 9 without mechanical coupling between the guide device 10 for guiding a surgical instrument through and the structural apparatus 4 for realizing the second axis of rotation. According to this embodiment, the tilting movements about the axes of rotation 3 and 6 created by means of the drive units 1 and 5 are not transferred mechanically to the pivot point 13. In this embodiment, the leadthrough 10 functions as floating bearing within the abdominal wall 14 as is also the case in manual laparoscopy with manually guided instruments. In this embodiment, the orientation of the instrument axis between the pivotal point 56 of the instrument drive unit 15 and the pivotal point of the guide device 10 results in the abdominal wall 14. The pivot point 13 in or on the abdominal wall 14 arises from the force resulting between torque exerted from outside and restoring or holding torque of the abdominal wall. This is gentler for the tissue of the abdominal wall, in particular when more than one instrument 9 is used each in its own guide device 10, since no direct fixed mechanically coupled force effect arises, by means of the coupling element 12, on the guide device 10 and thus on the abdominal wall 14.

The telescopic extension 8 serves to displace the instrument 9 through the guide device 10 along the instrument axis. The translatory motion is effected by displacing at least two, preferably three, telescopic elements 8u, 8v, 8w in relation to each other by means of an actuating drive 81 and adjusting elements 82, 83, preferably designed as toothed belts. The instrument 9 is mounted pivotably on the outermost telescopic element 8w in the instrument pivotal point 56 by means of the instrument drive unit 15.

The resulting instrument axis 11 of the instrument 9 is not identical to the telescopic longitudinal axis 58 because of the force transmission point 55 of the thrust device 5 on the telescopic extension 8. Because of the pivotable arrangement of the instrument drive unit 15 on the outermost telescopic extension 8w and the pivot and compensating movement about the instrument pivotal point 56 which is thus possible, neither the force transmission point 55 nor the pivotal point 6 of the coupling element 7 need lie on the instrument longitudinal axis 11. In particular, the pivotable arrangement of the instrument drive unit 15 about the instrument pivotal point 56 makes it possible for the instrument longitudinal axis 11 and the telescope longitudinal axis 58 to be variable with respect to each other, wherein the force transmission point 55 and the instrument pivotal point 56 are different and influence each other.

The omission of the coupling element 12 makes it is possible to guide two surgical instruments 9 through a shared leadthrough 10 by means of two manipulator arms according to the invention, and represents a significant improvement and increased flexibility vis-à-vis the state of the art.

Figure 5A:
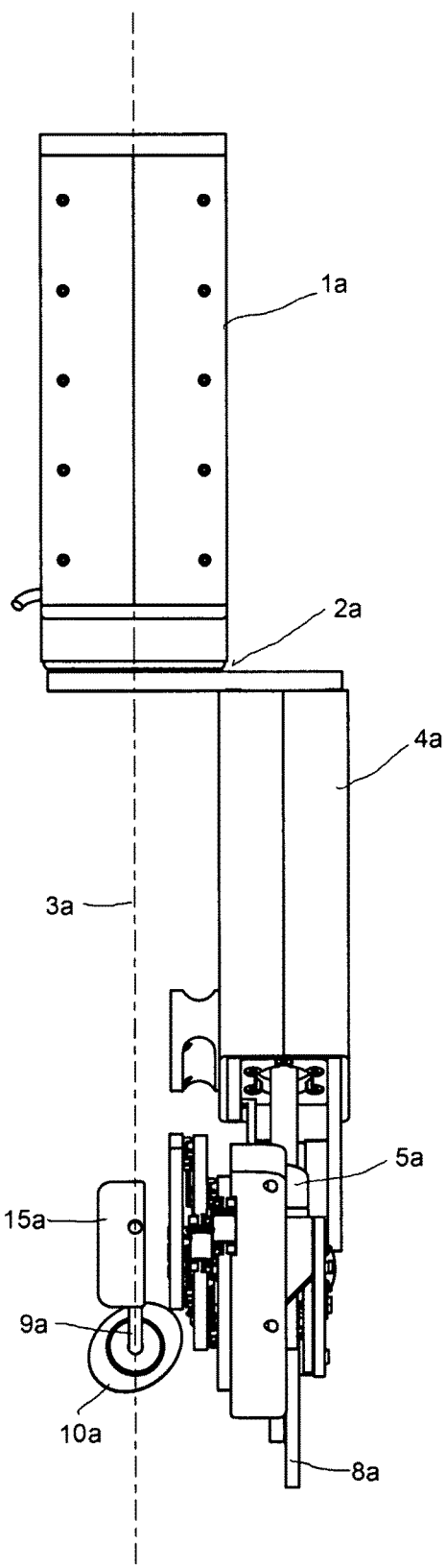
FIG. 5a is a top view of the manipulator arm according to the invention for the active positioning of a surgical instrument in the embodiment telescopic arm on the right.
Figure 5B:
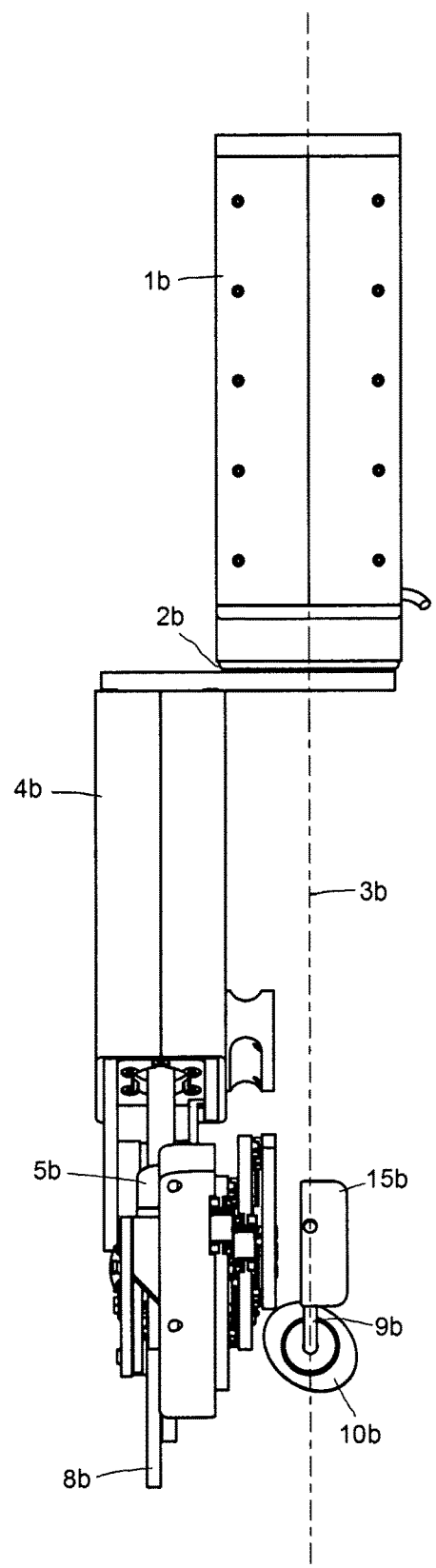
FIG. 5b is a top view of the manipulator arm according to the invention for the active positioning of a surgical instrument in the embodiment telescopic arm on the left.

FIGS. 5a and 5b show a top view of two different embodiments of the manipulator arm according to the invention for the active positioning of a surgical instrument. The structural design can be used preferably in a "right-handed" or "left-handed" embodiment. Starting from the first drive unit 1a, 1b with the pivot joint 2a, 2b, the second drive unit 4a can lie to the right of the axis of rotation 3a—right-handed embodiment—or the second drive unit 4b can lie to the left of the axis of rotation 3b—left-handed embodiment. The rotational movement orthogonal to the axis of rotation 3a, 3b is created analogously by the drive unit 5a, 5b. The surgical instrument 9a, 9b is moved along its instrument longitudinal axis through the leadthrough 10a, 10b by the telescopic extension 8a, 8b. The surgical instrument 9a, 9b itself is mechanically connected to the telescopic extension 8a, 8b by means of an instrument drive unit 15a, 15b.

Figure 6:
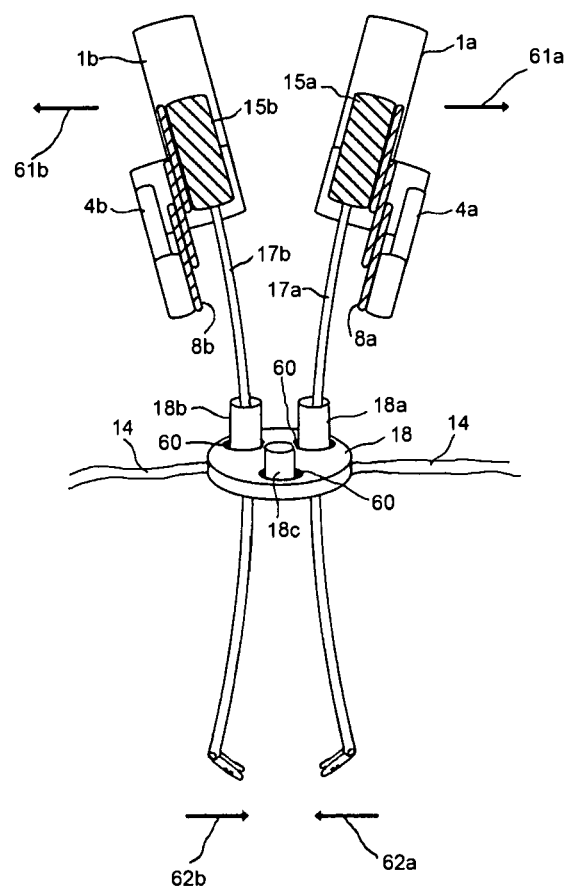
FIG. 6 is a schematic view of the manipulator arm according to the invention for the active positioning of a surgical instrument in the embodiments telescopic arm on the right and telescopic arm on the left for shared use with a single-port trocar.

FIG. 6 shows the use of two manipulator arms according to the invention for the active positioning of a surgical instrument in the "left-handed" and "right-handed" embodiments for shared use with a single-port trocar 18 with leadthroughs 18a, 18b, 18c. Preferably, curved instruments 17a, 17b are used in this configuration combined with a left-hand side manipulator arm 1b, 4b, 8b and a right-hand side manipulator arm 1a, 4a, 8a with the advantage that the surgical instruments 17a, 17b can be used through a shared trocar 18—which makes access through the abdominal wall 14 of the patient possible—and in each case separate leadthroughs 18a, 18b of the shared trocar 18. The separate leadthroughs 18a, 18b and 18c of the shared trocar 18 are mounted through an elastic material 60 so as to be tiltable in a movable manner relative to the trocar 18. As it is also possible to use the manipulator arm according to the invention without the mechanical coupling 12 between the holding element 4 on the manipulator arm and the pivot point 13 (see FIG. 1a) it is possible for only one trocar 18 with at least two leadthroughs 18a, 18b to be used. By the use of a left-hand side manipulator arm 1b, 4b, 8b according to the invention and of a right-hand side manipulator arm 1a, 4a, 8a according to the invention the danger of collision between the manipulator arms can be minimized because of the pivotal tilting movements.

Because of the preferable use of curved instruments 17a and 17b in a single-port trocar 18, a relative movement 62a, 62b of the two instruments towards each other, e.g. in order in the operating area to join tissue by means of a stitch, leads to a relative movement 61a, 61b away from each other of the two manipulator arms lying outside the patient. Thus, no collision can take place between the manipulator arms.

The use of crossed instruments in the single-port operating technique is known from the state of the art. In contrast to that, the embodiment present here as a matter of principle has the advantage of the avoidance of collisions when the tips of the instruments are brought together or moved onto one another in the body of the patient.

Figure 7:
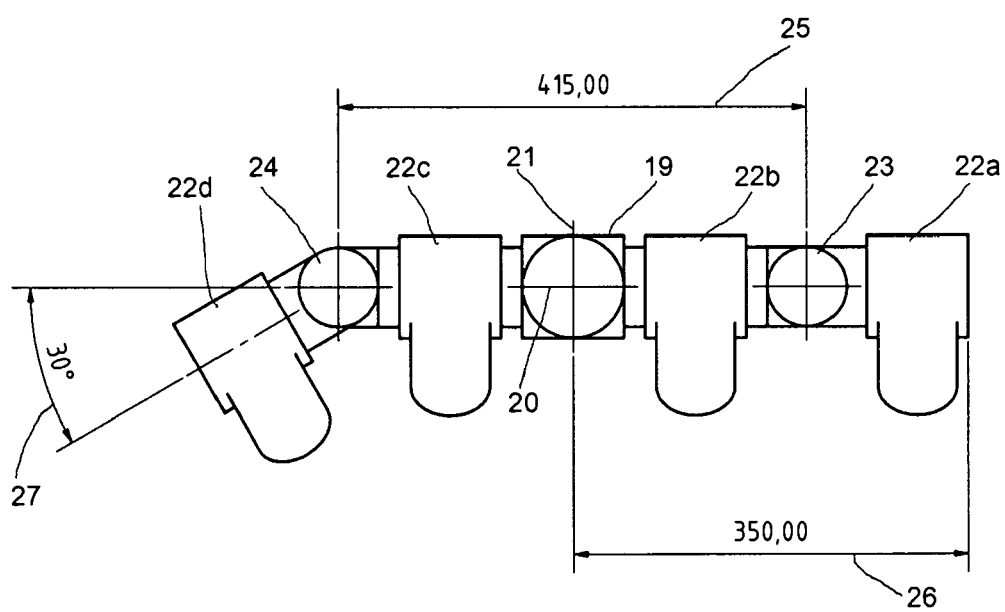
FIG. 7 is a schematic view of the flexibly adjustable support structure according to the invention.

FIG. 7 shows the structural design of a flexible support system or holding support system 19-26 for preferably up to four pre-positioning devices and manipulator arms. The flexible support system can be held via a coupling point 19 on a superordinate carrier system such that the flexible support system can be adjusted about the axis of rotation 20 by at least ±90° into an optimal position. The flexible support system preferably consists of four coupling points 22a-6d for adapting up to four pre-positioning devices. The outer coupling points 22a, 22d are connected by the joints 23, 24 to the coupling points 22b, 22c such that they can be tilted by up to 30° relative to the axis 20. The overall structural design is kept to an optimized minimum installation space 25, 26 of approximately 415 mm and 350 mm, respectively, as an exemplary embodiment and it can preferably be designed such that, for example, the width of the flexible support system can be 700 mm at most.

Figure 8:
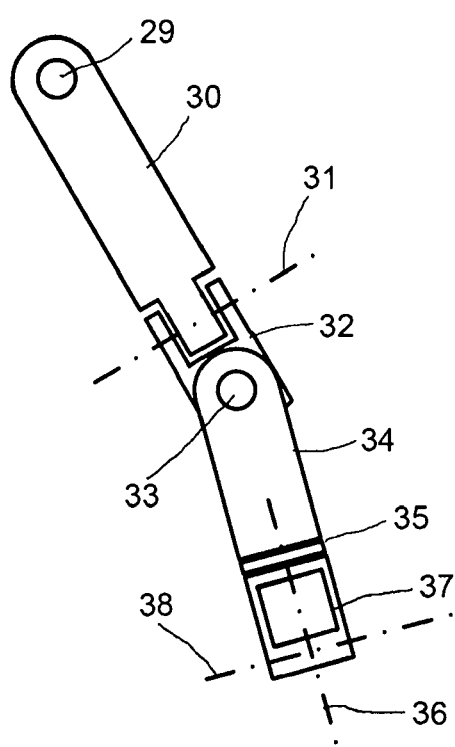
FIG. 8 is a schematic view of the pre-positioning device according to the invention.

FIG. 8 shows a pre-positioning device 29-38 according to the invention for adapting to a flexible support system (FIG. 7) and for receiving a manipulator arm according to the invention (FIGS. 1-4). The pre-positioning device is attached to a coupling point (e.g., 22d) of the flexible support system by means of a coupling joint 29 and makes it possible to rotate a first pre-positioning element 30 by preferably ±90° relative to the flexible support system, or the coupling point (e.g., 22d). A second pre-positioning element 32 is arranged via a further joint 31 to be rotatable by a further ±90° relative to the first pre-positioning element 30. The axes of rotation of the coupling point 29 and the joint 31 are preferably arranged orthogonal to each other. The second pre-positioning element 32 is connected via a further joint 33 to a third pre-positioning element 34 such that the third pre-positioning element 34 is held so as to be rotatable by ±90° relative to the second pre-positioning element 32. The third pre-positioning element 34 is connected via a pivot joint 35 to a fourth pre-positioning element 37. The axis of rotation 36 preferably lies in each case orthogonal to the axis of rotation of the joint 31 and 33 and makes possible rotational movements by ±90°. The fourth pre-positioning element 37 has a coupling point which makes possible a rotational movement about the axis of rotation 38, orthogonal to the axis of rotation 36. The manipulator arm according to the invention is coupled to the axis of rotation 38, as shown in FIGS. 1, 2, 3, 4, 5a and 5b.

Figure 9:
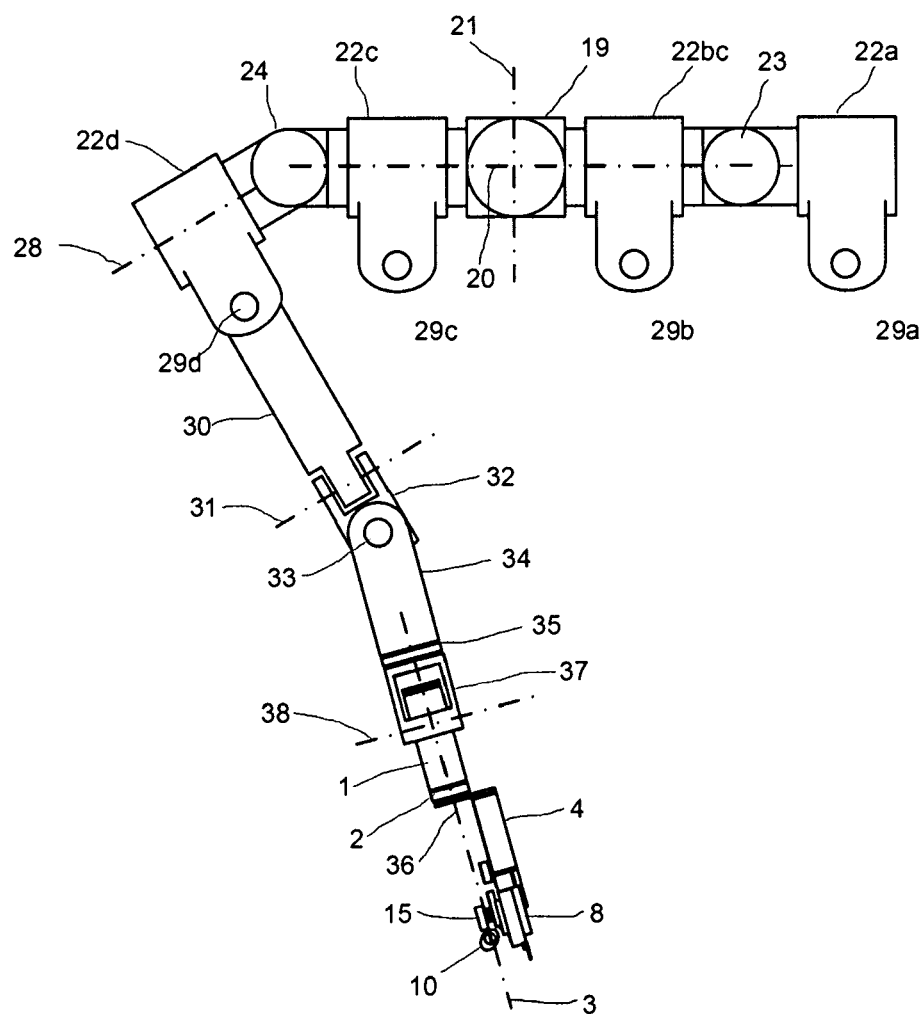
FIG. 9 is a schematic view of the flexibly adjustable support structure according to the invention with an attached pre-positioning device according to the invention to which is fixed a manipulator arm according to the invention for the active positioning of a surgical instrument.

FIG. 9 shows a preferred embodiment for connecting the flexible holding and support system 19-26 according to the invention to a pre-positioning device 29-38 according to the invention with, by way of example, a manipulator arm 1, 2, 3, 4, 8, 10, 15 according to the invention coupled thereon. The drive unit 1 of the manipulator arm is connected to the fourth pre-positioning element 37 of the pre-positioning device in the axis of rotation 38. The structural design is designed such that optionally either a left-handed or a right-handed embodiment of the manipulator arm according to the invention can be connected to the axis of rotation 38 of the pre-positioning device.

Figure 10:
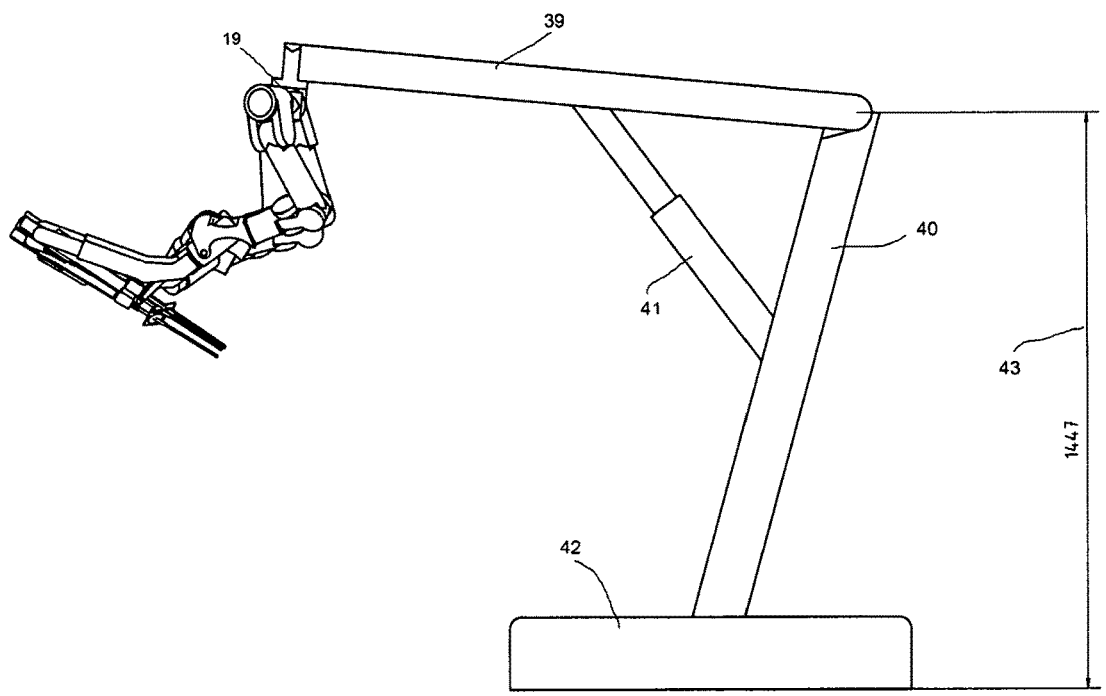
FIG. 10 is a schematic side view of a superordinate carrier system to which is fixed the flexibly adjustable support system according to the invention with a total of four attached pre-positioning devices according to the invention to which is fixed in each case a manipulator arm according to the invention for the active positioning of a surgical instrument.
Figure 11:
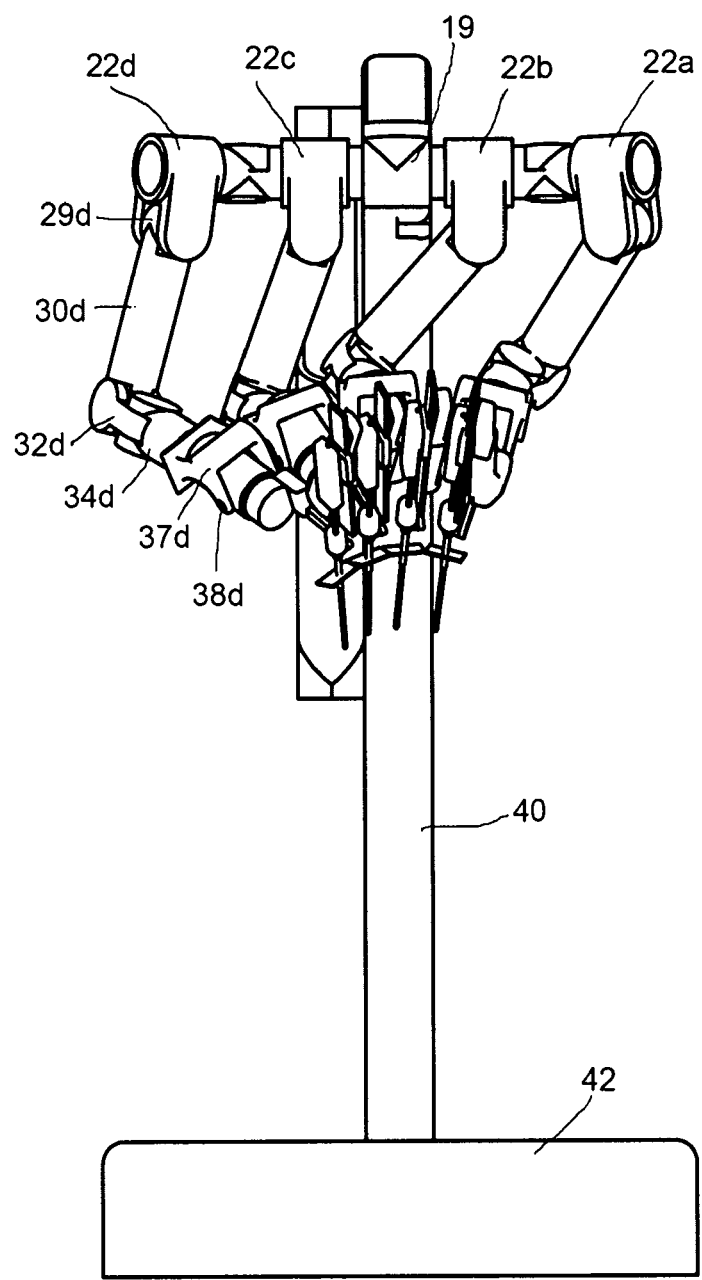
FIG. 11 is a schematic front view of the superordinate carrier system to which is fixed the flexibly adjustable support system according to the invention with a total of four attached pre-positioning devices according to the invention to which is fixed in each case a manipulator arm according to the invention for the active positioning of a surgical instrument.

FIG. 10 and FIG. 11 show a structural embodiment of the robotic surgical system according to the invention and in particular of the superordinate carrier system 39-43 to which the flexibly adjustable support system 22a-22d according to the invention is coupled by means of the coupling point or coupling support connection 19. The superordinate carrier system makes possible the optimal pre-positioning of the flexible support system 22a-22d by a horizontal alignment of the base support or locating bearing 42, which is preferably designed to be mobile, to the operating table 48 (see FIG. 12) and a vertical alignment by setting an optimal angle between groups of components 39 and 40 by the adjusting element 41. The pre-positioning device 29d-38d according to the invention is fixed on the flexible support system according to the invention via the coupling point 29d and receives the manipulator arms according to the invention at the coupling point 38d. The whole structural design is characterized vis-à-vis the state of the art by all the robotic components being concentrated in the manipulator arm and therefore, compared with the state of the art, the whole structural design requires significantly less installation space and in particular has a height 43 of, for example, only 1447 mm.

Figure 12:
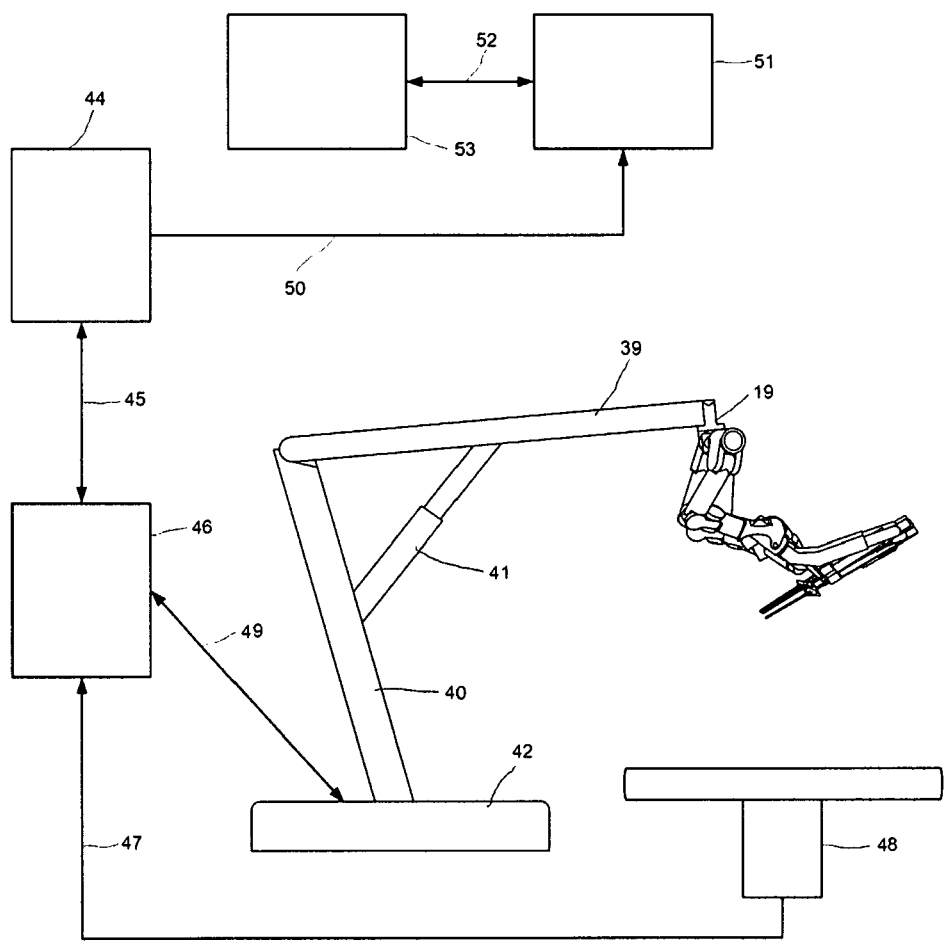
FIG. 12 is a schematic total view of the use of the superordinate carrier system in a robotic surgical system for use in minimally invasive surgery, such as e.g. laparoscopy.

FIG. 12 shows a schematic total view of the use of the superordinate carrier system 39-42 in a robotic surgical system for use in minimally invasive surgery, such as, e.g., laparoscopy. Starting from an operating unit 44, the user can transmit control commands for the actuating elements of the manipulator arm according to the invention to a control unit 46 via a suitable data connection 45. The control unit is connected via a further data line 49 to the superordinate carrier system 39-42 and, equipped with a carrier arm or main support device 39, 40, a flexible support system attached via the coupling point 19 can be pre-positioned via the coupling point 19 according to the position of the patient on the operating table 48 such that the flexible support system in conjunction with the pre-positioning devices makes possible an optimal positioning of the manipulator arms.

If a manipulator arm according to the invention is equipped with, e.g., an endoscopic camera, the image signals can be supplied via suitable data connections 49, 45, 50 to a processing unit 51 which processes the image data for display and supplies them via a further data connection 52 to a visualization unit 53. The visualization unit 53 can display both 2D and 3D image data, for example separately but also combined in a single image or a single image sequence. The control of how to display which image data is carried out by the control unit 44 according to the wish of the operator or surgeon. The control commands generated by the control unit 44 for this purpose are transmitted to the processing unit 51 by means of the data connection 50.

According to a further embodiment, the apparatus according to the invention is designed such that an instrument guide device is attached to the telescopic device, by which the surgical instrument is guided in a plane transverse to the longitudinal extension, wherein in particular the instrument guide device has a guide opening for the variable positioning of the surgical instrument. The additional instrument guide device is attached to the telescopic device, through which the shaft of the surgical instrument and/or endoscope extends. This additional instrument guide device is rigidly connected to the telescopic device. The surgical instrument and/or endoscope is positively driven by this additional instrument guide device about the first axis of rotation when the manipulator arm is rotated. Because of the structural design of the additional instrument guide device the positive drive only takes place for movements of the manipulator arm about the first axis of rotation. When the manipulator arm is rotated about the second axis of rotation, the additional instrument guide device makes possible a free movement of the surgical instrument and/or endoscope such that a resulting instrument axis arises from the rotation of the instrument drive unit on the telescopic device and the position of a first guide device (trocar), through which the surgical instrument and/or telescope extends.

Figure 13A:
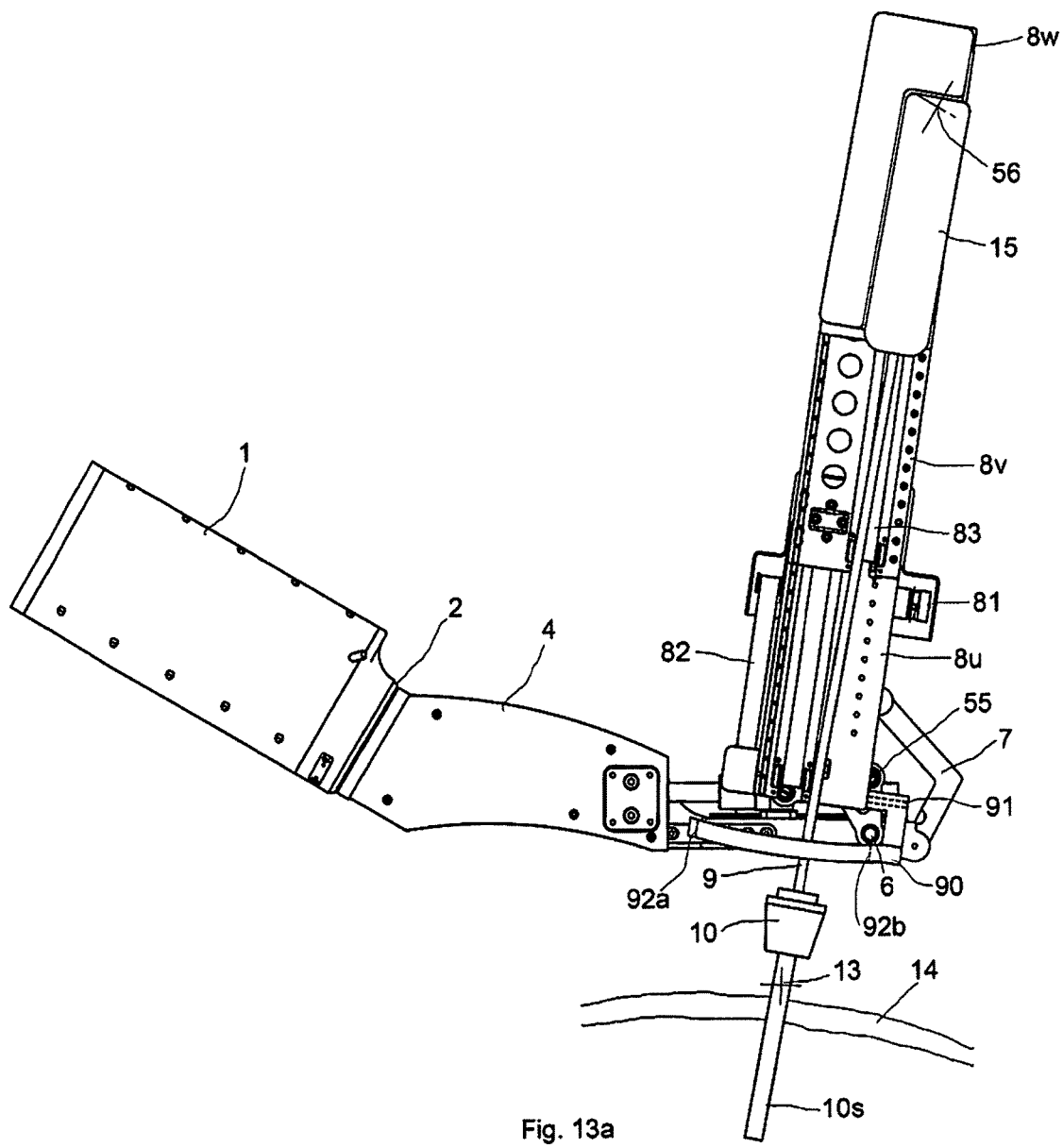
FIG. 13a is a schematic view of the manipulator arm on which an instrument guide device according to the invention is attached to the telescopic extension.
Figure 13B:
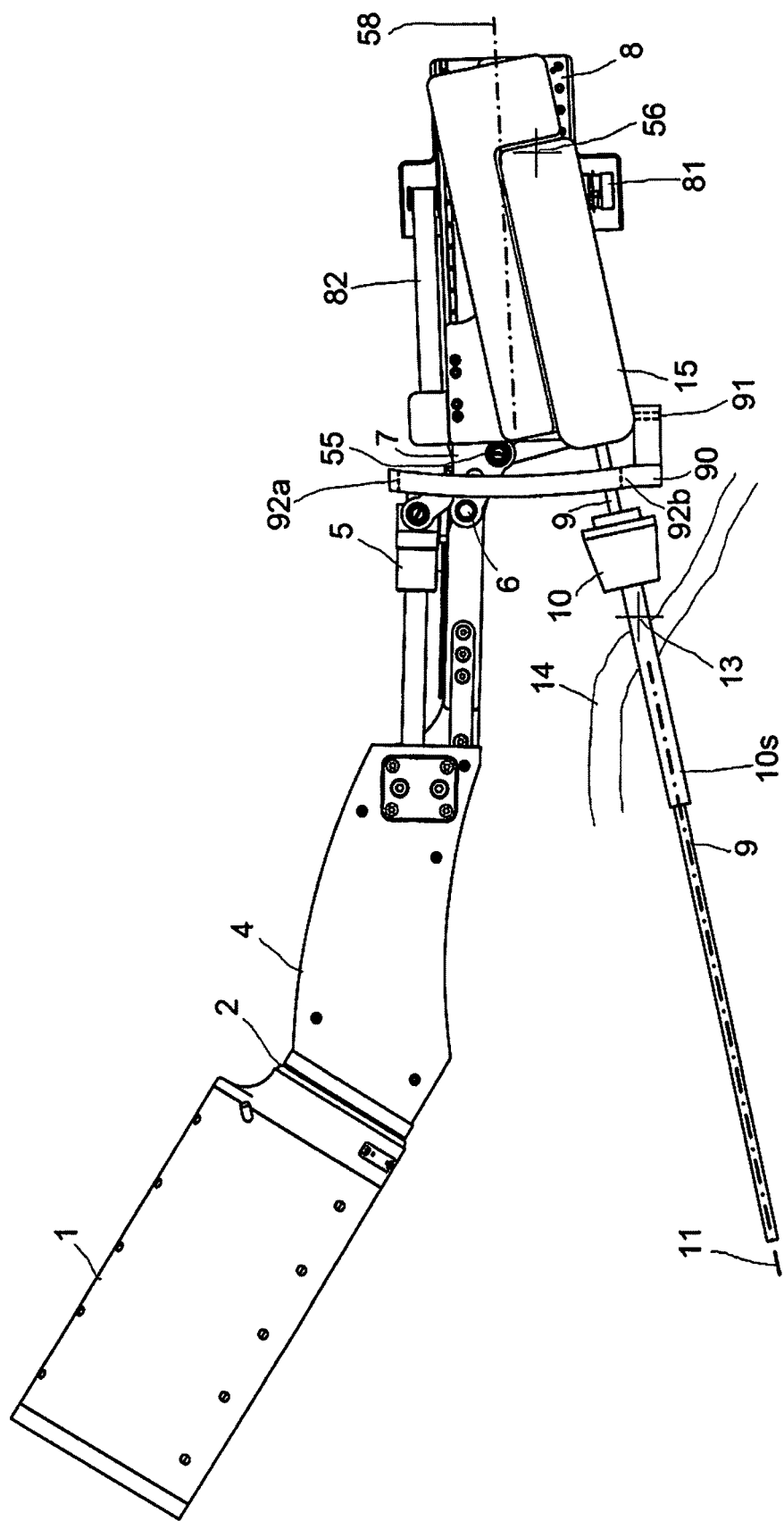
FIG. 13b is a further schematic view of the manipulator arm from FIG. 13a in another angular position, on which an instrument guide device according to the invention is attached to the telescopic extension.

FIGS. 13a, 13b, 14a, 14b, 15a, 15b show a manipulator arm according to the invention for the active positioning of a surgical instrument 9 without mechanical coupling between the guide device 10 for guiding a surgical instrument 9 through and the structural apparatus 4 for realizing the second axis of rotation. FIGS. 13a and 13b show an embodiment of the invention which corresponds substantially to that of FIGS. 3a and 3b with an instrument guide device 90.

The instrument guide device 90 is attached on the telescopic extension 8 by means of a releasable fixing apparatus 91 in particular in the form of a screw such that, on rotation of the manipulator arm about a first axis of rotation (rotation of the pivot joint 2), the surgical instrument 9 is positively guided through or within the instrument guide device 90. The instrument guide device 90 is structurally designed such that the surgical instrument 9, on tilting of the manipulator arm about a second axis of rotation 2 (rotation about the pivotal point 6), can displace freely in an axis within the instrument guide device 90 in a longitudinal opening 92 between the limitations 92a and 92b of the longitudinal opening 92, with the result that a resulting alignment of the longitudinal axis of the surgical instrument 9 without positive drive from the instrument pivotal point 56 and the guide device 10 results.

This solution has the advantage that, when a surgical instrument 9 is rotated about a first axis of rotation (rotation about the pivot joint 2), the surgical instrument 9 is positively driven and the instrument guide device 90 used for the positive drive the forces acting on the surgical instrument 9 in the direction of the axis of rotation 6 are absorbed without having to mechanically couple or connect the instrument leadthrough 10 to the manipulator arm.

FIG. 13b illustrates that the instrument 9 can pivot freely in the instrument guide device 90 between the limitations 92a and 92b of the guide opening.

Figure 14A:
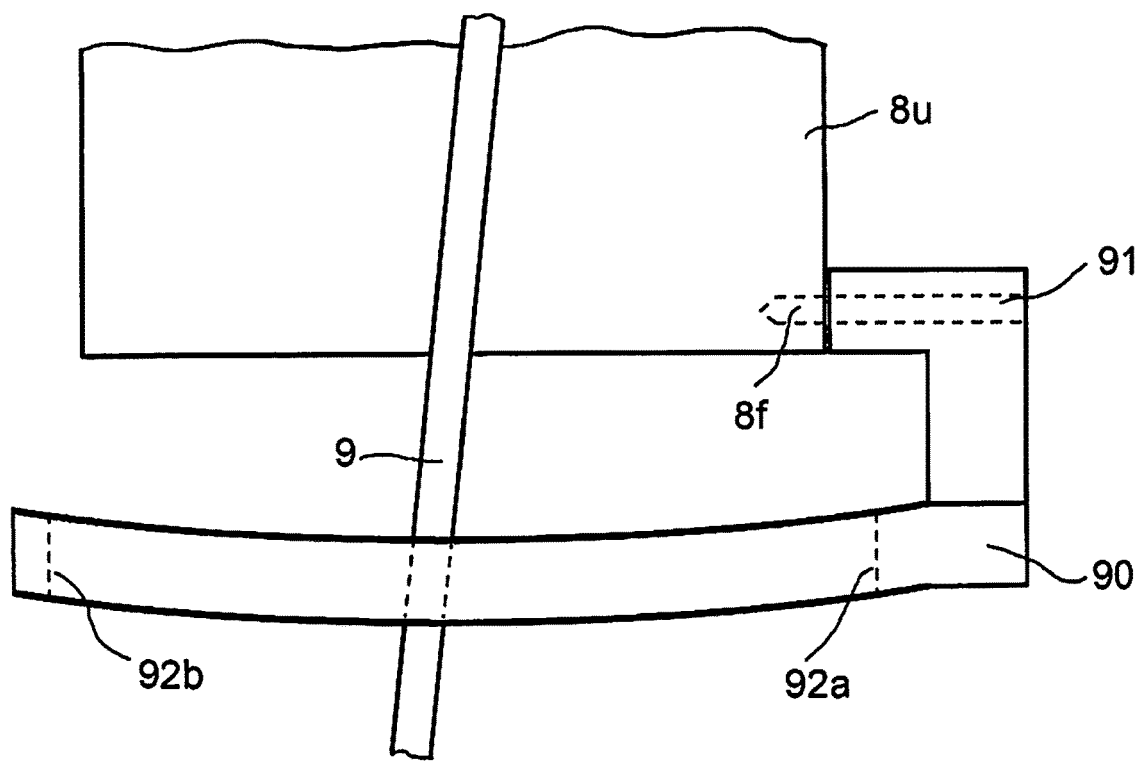
FIGS. 14a, 14b show schematically in section the embodiment from FIGS. 13a and 13b with regard to the coupling of the guide device 90.
Figure 14B:
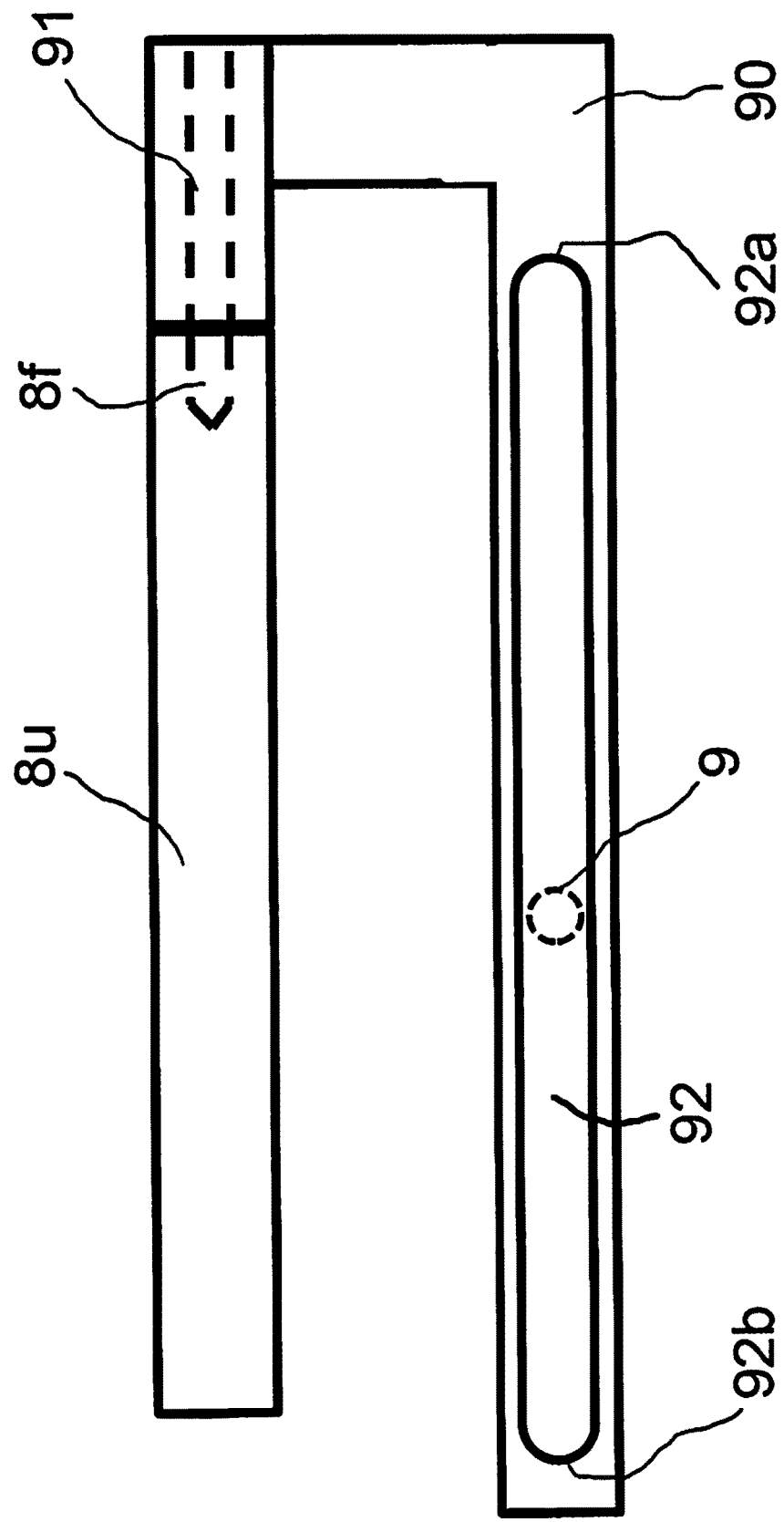

FIGS. 14a, 14b show schematically in section the embodiment from FIGS. 13a and 13b with the instrument guide device 90 which is fixed to the telescopic extension 8u by means of a screw, not shown, in the fixing apparatus 8f, 91, preferably designed as a releasable screw or plug-in connection. Moreover, the elongate guide opening 92 is represented with its lateral limitations 92a and 92b between which the surgical instrument 9 can be displaced.

Figure 15A:
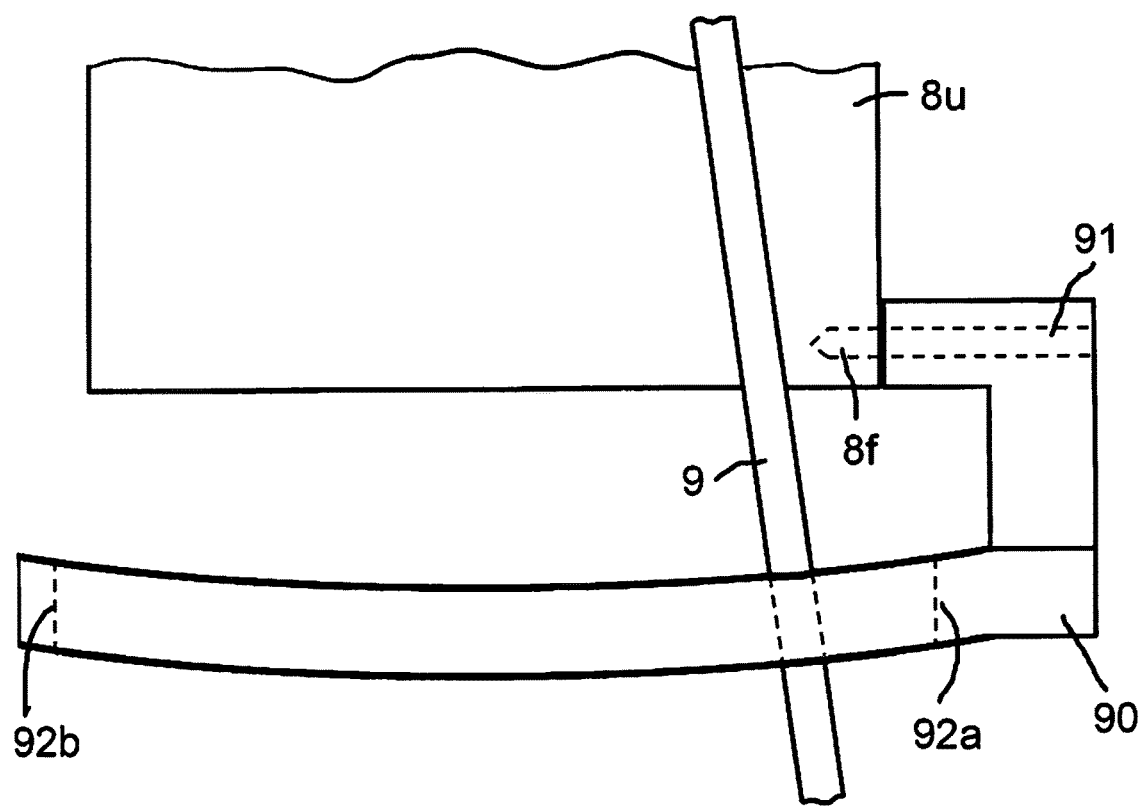
FIGS. 15a, 15b show a position of the surgical instrument displaced with respect to FIGS. 14a and 14b.
Figure 15B:
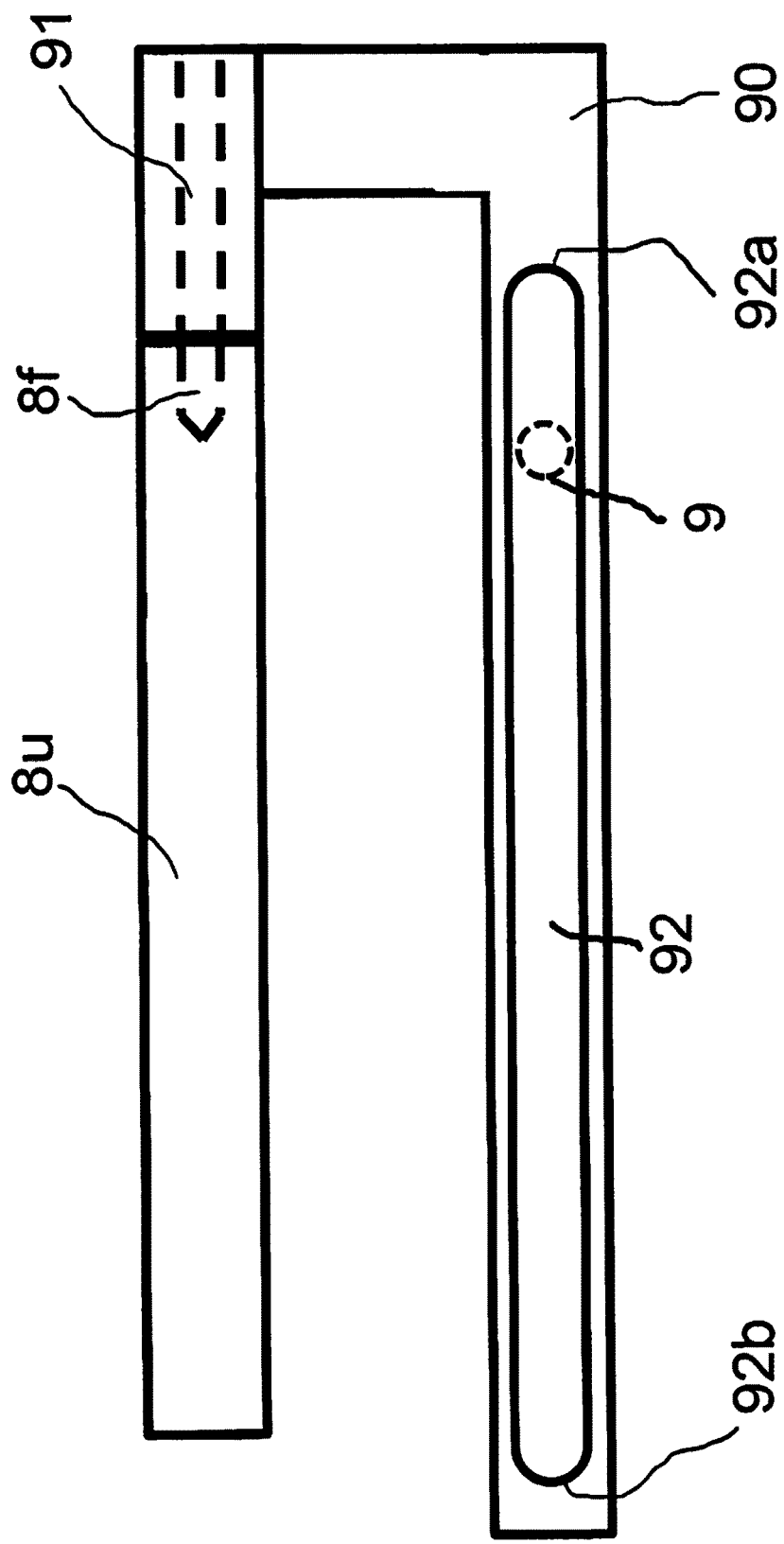

FIGS. 15a, 15b also show schematically the coupling of the instrument guide device 90 to the telescopic extension 8u for a further orientation of the surgical instrument 9 relative to the longitudinal axis of the telescope 8u, whereby it can be seen that the position of the surgical instrument 9 can be moved within the instrument guide device 90.

The embodiment of the invention according to FIGS. 13 to 15 with the instrument guide device 90 has the advantage in particular that there is no dependence on the mechanical load limit of the trocar or of the instrument leadthrough 10.

Moreover, the instrument guide device 90 makes it possible, by means of the still present decoupling of the longitudinal axis of the surgical instrument 9 from the longitudinal axis of the telescopic extension 8, for a resulting pivot point 13 to arise at the point at which the biomechanical stresses are lowest for the abdominal wall as a result of the tilting away of the instrument guide 10.

The present invention thus relates on the one hand to a holding and positioning apparatus for a surgical instrument and/or an endoscope, wherein one or more such holding and positioning apparatuses according to the invention are attached to a robotic surgical system in each case via coupling points, wherein these coupling points are in turn connected to each other in each case, with the result that the installation space required by the robotic surgical system is advantageously only very small. The particularly compact construction also results from the particularly simple and compact practicability of the holding and positioning apparatus according to the invention, wherein the latter can furthermore also be retrofitted to an existing robotic system.

In a preferred embodiment, the guide device for guiding a surgical instrument through is rigidly connected via a coupling element to the structural apparatus for creating the second axis of rotation. The rotational movement of the axis of rotation 1 thus leads to a positive movement of the guide device for guiding a surgical instrument through about the invariant point in a direction x.

In a further preferred embodiment, the guide device for guiding a surgical instrument through is not structurally rigidly connected to the structural apparatus for creating the second axis of rotation. The guide device for guiding a surgical instrument through thus functions as a floating bearing in the abdominal wall as is usual in manual laparoscopy.

In a further preferred embodiment, the surgical instrument is coupled to the telescopic apparatus via an instrument drive unit which comprises a rotary actuator by means of which the shaft of the surgical instrument is rotatably varied about the z direction relative to the starting position. The instrument drive unit preferably has three instrument actuators by which the operative unit of the surgical instrument attached to the distal end is variable in three further degrees of freedom. Particularly preferably, the instrument drive unit is arranged via a holding device to be rotatable at the proximal end of the telescopic system.

The invention claimed is:

1. A holding and positioning apparatus of a surgical instrument for minimally invasive surgery, for use within a robotic surgical system, comprising:
    an instrument drive unit,
    a telescopic device with the surgical instrument fixed to the telescopic device by the instrument drive unit, wherein the surgical instrument can be moved by the telescopic device in a translational manner along an instrument longitudinal axis of the surgical instrument through a guide device into the body,
    a first drive unit comprising a first axis of rotation, about which a holding element is rotatably arranged, wherein the first axis of rotation always intersects with the instrument longitudinal axis of the surgical instrument at a pivot point,
    wherein a linear actuator is attached to the holding element, and the telescopic device is arranged on a coupling guide which is formed as a coupling joint, and wherein the linear actuator is formed to transmit power to the coupling guide at a linear actuator position point formed as a pivotal point,
    wherein the instrument drive unit is rotatably mounted on the telescopic device by an instrument pivotal point and wherein the coupling guide has a coupling point which is rigidly connected to the holding element and which defines a second axis of rotation orthogonal to the first axis of rotation and spaced apart from the first axis of rotation, such that by way of power transmission via the linear actuator to the coupling guide, a rotation of the coupling guide about the second axis of rotation can be realized, such that the instrument longitudinal axis of the surgical instrument is independently adjustable relative to a telescope longitudinal axis of the telescopic device in dependence on the linear actuator and such that the instrument drive unit is rotatable around an axis orthogonal to the first axis of rotation around the pivot point.

2. The holding and positioning apparatus according to claim 1, wherein the telescopic device has several telescopic elements, and the instrument pivotal point is arranged on the telescopic element which has the largest telescopic adjustability.

3. The holding and positioning apparatus according to claim 1, wherein the guide device has at least one instrument guide through which a shaft of the surgical instrument extends.

4. The holding and positioning apparatus according to claim 1, wherein the instrument drive unit moves the surgical instrument in several degrees of freedom, and wherein the instrument drive unit is controlled by a surgeon via a control unit by way of control and supply lines which are guided through the holding element and the linear actuator.

5. The holding and positioning apparatus according to claim 1, wherein the first axis of rotation is formed in that a drive unit is provided which can be attached to a robotic arm, wherein a pivot joint is provided between the drive unit and the holding element.

6. The holding and positioning apparatus according to claim 1, wherein a coupling element is attached to the holding element, which is rotatably connected to the instrument guide at a distal end at the pivot point.

7. The holding and positioning apparatus according to claim 1, wherein several surgical instruments are guided into the inside of the body through a single trocar, and a separate instrument drive unit is provided for each surgical instrument, and in particular the surgical instruments are formed curved in the longitudinal direction.

8. The holding and positioning apparatus according to claim 1, wherein the holding element and/or the drive unit can be adapted in its starting position by means of a pre-positioning device, wherein the pre-positioning device has one or more pre-positioning elements, which in each case can be pre-set in their position via at least one axis of rotation, wherein in particular four pre-positioning elements can be pre-set with positions which are variable with respect to each other in series.

9. The holding and positioning apparatus according to claim 1, wherein an instrument guide device is attached to the telescopic device, by means of which the surgical instrument is guided in a plane transverse to a longitudinal extension, and the instrument guide device in particular has a guide opening for variable positioning of the surgical instrument.

10. A robotic surgical system with several holding and positioning apparatuses according to claim 1, wherein at least two holding and positioning apparatuses are attached to a holding support system running substantially transverse to the holding and positioning apparatuses, wherein the holding support system is constructed in each case from a coupling point for each holding and positioning apparatus, and wherein the coupling points in each case are connected to each other either rigidly or via joints.

11. The robotic surgical system according to claim 10, wherein the holding support system is connected by means of a coupling support connection to a substantially vertically running main support device for support in relation to a fixed bearing, which is arranged to be movable or is predefined with respect to a fixed or mobile operating table.

12. The robotic surgical system according to claim 10, wherein a central control unit is provided which is connected to each of the holding and positioning apparatuses with the corresponding surgical instruments and/or endoscopes and is coupled to an operating unit for the input of commands in the form of control data of a surgeon, which operating unit displays image data from one or more endoscopes by a visualization unit.

13. The robotic surgical system according to claim 10, wherein the control unit and the operating unit are coupled to a mobile operating table, and both the image data and the control data are processed in dependence on predetermined positions of the holding and positioning apparatus as well as of the operating table.

\* \* \* \* \*